(12) United States Patent
Engelbart et al.

(10) Patent No.: US 9,645,095 B2
(45) Date of Patent: May 9, 2017

(54) SYSTEM AND METHOD FOR INSPECTING A COMPOSITE PART DURING MANUFACTURE

(71) Applicant: The Boeing Company, Chicago, IL (US)

(72) Inventors: Roger W. Engelbart, St. Louis, MO (US); James W. Fonda, Summerville, SC (US); Allen Halbritter, North Charleston, SC (US)

(73) Assignee: The Boeing Company, Chicago, IL (US)

( * ) Notice: Subject to any disclaimer, the term of this patent is extended or adjusted under 35 U.S.C. 154(b) by 169 days.

(21) Appl. No.: 14/507,241

(22) Filed: Oct. 6, 2014

(65) Prior Publication Data

US 2016/0097728 A1    Apr. 7, 2016

(51) Int. Cl.
*G01N 21/88* (2006.01)
*B29C 70/38* (2006.01)
(Continued)

(52) U.S. Cl.
CPC ......... *G01N 21/8851* (2013.01); *B29C 70/38* (2013.01); *B29C 70/54* (2013.01); *G05B 19/41875* (2013.01); *G05B 19/4207* (2013.01); *G01N 2021/8883* (2013.01); *G01N 2201/06113* (2013.01); *G01N 2201/102* (2013.01); *G05B 2219/37198* (2013.01); *Y02P 90/22* (2015.11); *Y02P 90/265* (2015.11)

(58) Field of Classification Search
None
See application file for complete search history.

(56) References Cited

U.S. PATENT DOCUMENTS 6,799,619 B2   10/2004   Holmes et al.
6,814,822 B2   11/2004   Holmes et al.
(Continued)

OTHER PUBLICATIONS

"Digital Camera Based Composite Damage Mapping," [online] [retrieved Nov. 24, 2014]. Retrieved from the Internet: <http://www.nlign.com/wp-content/uploads/2012/11/NLign-Analytics-DIGITAL-CAMERA-BASED-COMPOSITE-DAMAGE-MAPPING.pdf>. 2012, 1 page.
(Continued)

*Primary Examiner* — Kara E Geisel
*Assistant Examiner* — Amanda Merlino
(74) *Attorney, Agent, or Firm* — Alston & Bird LLP

(57) ABSTRACT

A method, system and computer-readable storage medium are provided to facilitate inspection of a composite part during manufacture. In the context of a system, a system for inspecting a composite part during manufacture is provided that includes an inspection system configured to detect an in-process anomaly with respect to a ply of the composite part during placement of the ply. The system also includes a computing system configured to determine part location coordinates of the in-process anomaly detected by the inspection system with respect to the ply of the composite part. The computing system is also configured to map the in-process anomaly to a digital part model based upon the part location coordinates. The system additionally includes a display, responsive to the computing system, configured to present a representation of the digital part model including an indication of the in-process anomaly relative thereto.

17 Claims, 3 Drawing Sheets

(51) Int. Cl.
 B29C 70/54 (2006.01)
 G05B 19/42 (2006.01)
 G05B 19/418 (2006.01)

(56) References Cited

U.S. PATENT DOCUMENTS

| | | | |
|---|---|---|---|
| 6,871,684 B2 | 3/2005 | Engelbart et al. |
| 7,039,485 B2 | 5/2006 | Engelbart et al. |
| 7,171,033 B2 | 1/2007 | Engelbart et al. |
| 7,193,696 B2 | 3/2007 | Engelbart et al. |
| 7,236,625 B2 | 6/2007 | Engelbart et al. |
| 7,289,656 B2 | 10/2007 | Engelbart et al. |
| 7,362,437 B2 | 4/2008 | Engelbart et al. |
| 7,372,556 B2 | 5/2008 | Engelbart et al. |
| 7,424,902 B2 | 9/2008 | Engelbart et al. |
| 7,435,947 B2 | 10/2008 | Engelbart et al. |
| 7,489,392 B2 | 2/2009 | Engelbart et al. |
| 7,513,964 B2 | 4/2009 | Ritter et al. |
| 7,576,850 B2 | 8/2009 | Engelbart et al. |
| 7,678,214 B2 | 3/2010 | Engelbart et al. |
| 7,688,434 B2 | 3/2010 | Engelbart et al. |
| 7,712,502 B2 | 5/2010 | Engelbart et al. |
| 7,769,224 B2 | 8/2010 | Engelbart et al. |
| 7,807,002 B2 | 10/2010 | Engelbart et al. |
| 7,889,907 B2 | 2/2011 | Engelbart et al. |
| 7,978,328 B2 | 7/2011 | Engelbart et al. |
| 7,983,469 B2 | 7/2011 | Engelbart et al. |
| 8,068,659 B2 | 11/2011 | Engelbart et al. |
| 8,184,281 B2 | 5/2012 | Engelbart et al. |
| 8,668,793 B2 | 3/2014 | Engelbart et al. |
| 8,836,934 B1* | 9/2014 | Safai ........................ G06T 7/001 356/237.3 |
| 2006/0108948 A1 | 5/2006 | Shin et al. |
| 2007/0277919 A1 | 12/2007 | Savol et al. |
| 2008/0277042 A1 | 11/2008 | Engelbart et al. |
| 2009/0169056 A1 | 7/2009 | Engelbart et al. |
| 2010/0204929 A1 | 8/2010 | Engelbart et al. |
| 2010/0263505 A1 | 10/2010 | Engelbart et al. |
| 2011/0017380 A1 | 1/2011 | Engelbart et al. |
| 2012/0216957 A1 | 8/2012 | Engelbart et al. |
| 2013/0010309 A1 | 1/2013 | Engelbart et al. |
| 2014/0124142 A1 | 5/2014 | Engelbart et al. |

OTHER PUBLICATIONS

"NLign Analytics Introduction," [online] [retrieved Nov. 24, 2014]. Retrieved from the Internet: <http://www.nlign.com/wp-content/uploads/2012/10/NLign-Introduction.pdf. 2012, 16 pages.

"Revealing the Cause of Tool-Related Porosity with NLign," [online] [retrieved Nov. 24, 2014]. Retrieved from the Internet: <http://www.nlign.com/wp-content/uploads/2013/03/CaseStudy__Tool-Related-Porosity__03.13.13.pdf>. 2013, 2 pages.

"GE Intelligent Platforms: Proficy Historian 5.5," [online] [retrieved Nov. 24, 2014]. Retrieved from the Internet: <http://www.ge-ip.com/download/proficy-historian-5-5/12501/3701/>. 2013, 4 pages.

\* cited by examiner

SYSTEM AND METHOD FOR INSPECTING A COMPOSITE PART DURING MANUFACTURE

TECHNOLOGICAL FIELD

A system, method and computer-readable storage medium are provided in accordance with an example embodiment in order to inspect a composite part during manufacture and, more particularly, to detect an in-process anomaly and to display a representation of a digital part model including an indication of the in-process anomaly to facilitate the anomaly being addressed in a more timely manner.

BACKGROUND

A variety of parts may be formed of composite materials. For example, a variety of parts may be formed by composite plies that are laid up, such as upon a forming tool. Each composite ply may be formed of a plurality of fibers disposed within a resin matrix such that the properties of the resulting composite part may be tailored. By way of a more specific example, the fuselage of an aircraft may be formed of a plurality of plies of composite material that are laid up to form one or more barrel sections.

During the manufacture of a composite part, the plies are inspected to identify anomalies. A variety of anomalies may be identified including dropped tows, untacked tows, tow gaps, twists, overlaps and the presence of foreign object debris (FOD). In this regard, each ply may be inspected following its placement to identify anomalies that may be addressed prior to applying another ply thereover. In a number of instances, the inspection of the composite plies is performed manually with an inspector providing an indication of any anomaly that is detected, such as by circling the anomaly on the ply itself. Thereafter, the anomalies that have been identified may be studied and at least some of the anomalies may be addressed, such as by being repaired, depending upon the manufacturing specifications for the composite part that is being fabricated.

The manual inspection of each ply following its placement may be a time consuming process which may slow the overall manufacturing process for the composite part. In this regard, following the placement of a ply, an inspector must visually inspect the surface of the ply and, in an instance in which an anomaly is identified, the location of the anomaly is marked upon the ply. If it is determined that the anomaly is to be addressed, the anomaly may be repaired followed by a further manual inspection of the repaired ply prior to placing the next ply thereover.

For automated lamination systems, such as automated fiber placement or tape placement systems, vision systems have been utilized in order to inspect the plies. While automated lamination systems including vision systems may identify an anomaly, such systems have not generally been able to identify the location of the anomaly relative to the composite part that being manufactured or relative to other anomalies detected on the same or another ply. As such, although automated lamination systems including vision systems are useful in identifying anomalies during the manufacture of a composite part, challenges remain in regards to determining the manner in which each anomaly should be addressed. For example, the requirements for a composite part that dictate the manner in which various anomalies are to be addressed may vary depending upon the location of the anomaly with respect to the composite part and/or the relationship of the anomaly to other anomalies on the same or other plies of the composite part.

BRIEF SUMMARY

A method, system and computer-readable storage medium are provided according to an example embodiment to facilitate inspection of a composite part during manufacture. In this regard, the method, system and computer-readable storage medium may provide for the detection of an in-process anomaly during placement of a ply and the determination of the location of the in-process anomaly with respect to the composite part and, therefore, with respect to other plies of the composite part. Thus, a determination as to the manner in which the in-process anomaly should be addressed may be made in a more informed and timely manner. By facilitating the inspection of a composite part during manufacture and by correspondingly facilitating any repair of the composite part during manufacture, the composite part may be manufactured in a more timely and efficient manner, thereby improving the overall manufacturing process.

In an example embodiment, a method for inspecting a composite part during manufacture is provided that includes detecting an in-process anomaly with respect to a ply of the composite part during placement of the ply. The method of this embodiment also includes determining part location coordinates of the in-process anomaly with respect to the ply of the composite part. The method of this embodiment additionally includes mapping the in-process anomaly to a digital part model based upon the part location coordinates. Further, the method includes displaying a representation of the digital part model including an indication of the in-process anomaly relative thereto. As such, a technician may review the display of the digital part model including the indication of the in-process anomaly in the course of determining whether the in-process anomaly should be addressed.

The method of an example embodiment may detect the in-process anomaly by scanning a surface of the ply of the composite part during placement of the ply with a vision-based inspection system. The method of an example embodiment may determine the part location coordinates by obtaining machine axis coordinates of the in-process anomaly with respect to the ply of a composite part from a machine controller or a process parameter monitoring system. The method of this example embodiment also determines the part location coordinates by converting the machine axis coordinates to part location coordinates. The method of an example embodiment may map the in-process anomaly to the digital part model by providing the part location coordinates for the in-process anomaly to three-dimensional visualization software that overlays the representation of the in-process anomaly onto the digital part model.

In accordance with an example embodiment, the detection of the in-process anomaly may include determining a type of in-process anomaly. In this example embodiment, the display of the representation of the digital part model may include the assignment of different visual indications to different types of in-process anomalies. The method of an example embodiment may display additional information along with indications of the in-process anomalies. For example, the display of the representation of the digital part model may include overlaying post-cure quality data onto the digital part model concurrent with the indications of the in-process anomalies. Additionally or alternatively, the display of the representation of the digital part model may include overlaying in-process sensor measurement locations on to the digital part model concurrent with the indications of the in-process anomalies.

In another example embodiment, a system for inspecting a composite part during manufacture is provided that includes an inspection system configured to detect an in-process anomaly with respect to a ply of the composite part during placement of the ply. The system of this example embodiment also includes a computing system configured to determine part location coordinates of the in-process anomaly detected by the inspection system with respect to the ply of the composite part. The computing system is also configured to map the in-process anomaly to a digital part model based upon the part location coordinates. The system of this example embodiment also includes a display, responsive to the computing system, configured to present a representation of the digital part model including an indication of the in-process anomaly relative thereto.

The inspection system of an example embodiment includes a vision based inspection system configured to scan a surface of the ply of the composite part during placement of the ply. In an example embodiment, the computing system is configured to determine the part location coordinates by obtaining machine axis coordinates of the in-process anomaly with respect to the ply of the composite part from a machine controller or a process parameter monitoring system and to convert the machine axis coordinates to the part location coordinates. The computing system of an example embodiment may be configured to map the in-process anomaly to the digital part model by providing the part location coordinates for the in-process anomaly to three-dimensional visualization software that overlays the representation of the in-process anomaly onto the digital part model.

The computing system may be further configured to determine a type of in-process anomaly. In this example embodiment, the display is further configured to assign different visual indications to different types of in-process anomalies. The display of an example embodiment may be configured to display additional information concurrent with the indications of the in-process anomalies to further facilitate an efficient determination as to the manner in which the anomalies are to be addressed. For example, the display may be further configured to overlay post-cure quality data onto the digital part model concurrent with the indications of the in-process anomalies. Additionally or alternatively, the display may be further configured to overlay in-process sensor measurement locations onto the digital part model concurrent with the indications of the in-process anomalies.

In a further example embodiment, a non-transitory computer-readable storage medium for inspecting a composite part during manufacture is provided with a computer-readable storage medium having computer-readable program code portions stored therein that in response to execution cause a computing system to receive information regarding an in-process anomaly with respect to a ply of the composite part during placement of the ply. The computer-readable program code portions also cause the computing system to determine part location coordinates of the in-process anomaly with respect to the ply of the composite part and to map the in-process anomaly to a digital part model based upon the part location coordinates. The computer-readable program code portions of this example embodiment also cause the computing system to cause a representation to be presented of the digital part model including an indication of the in-process anomaly relative thereto.

The computer-readable program code portions that are configured to determine the part location coordinates may include computer-readable program code portions configured to obtain machine axis coordinates of the in-process anomaly with respect to the ply of the composite part from a machine controller or a process parameter monitoring system and to convert the machine axis coordinates to the part location coordinates. In an example embodiment, the computer-readable program code portions configured to detect the in-process anomaly may include computer-readable program code portions configured to determine a type of in-process anomaly. In this example embodiment, the computer-readable program code portions configured to display the representation of the digital part model may include computer-readable program code portions configured to assign different visual indications to different types of in-process anomalies. The computer-readable program code portions that are configured to display the representation of the digital part model may also include computer-readable program code portions configured to overlay post-cure data and/or in-process sensor measurement locations onto the digital part model concurrent with the indications of the in-process anomalies.

BRIEF DESCRIPTION OF THE DRAWINGS

Figure 1:
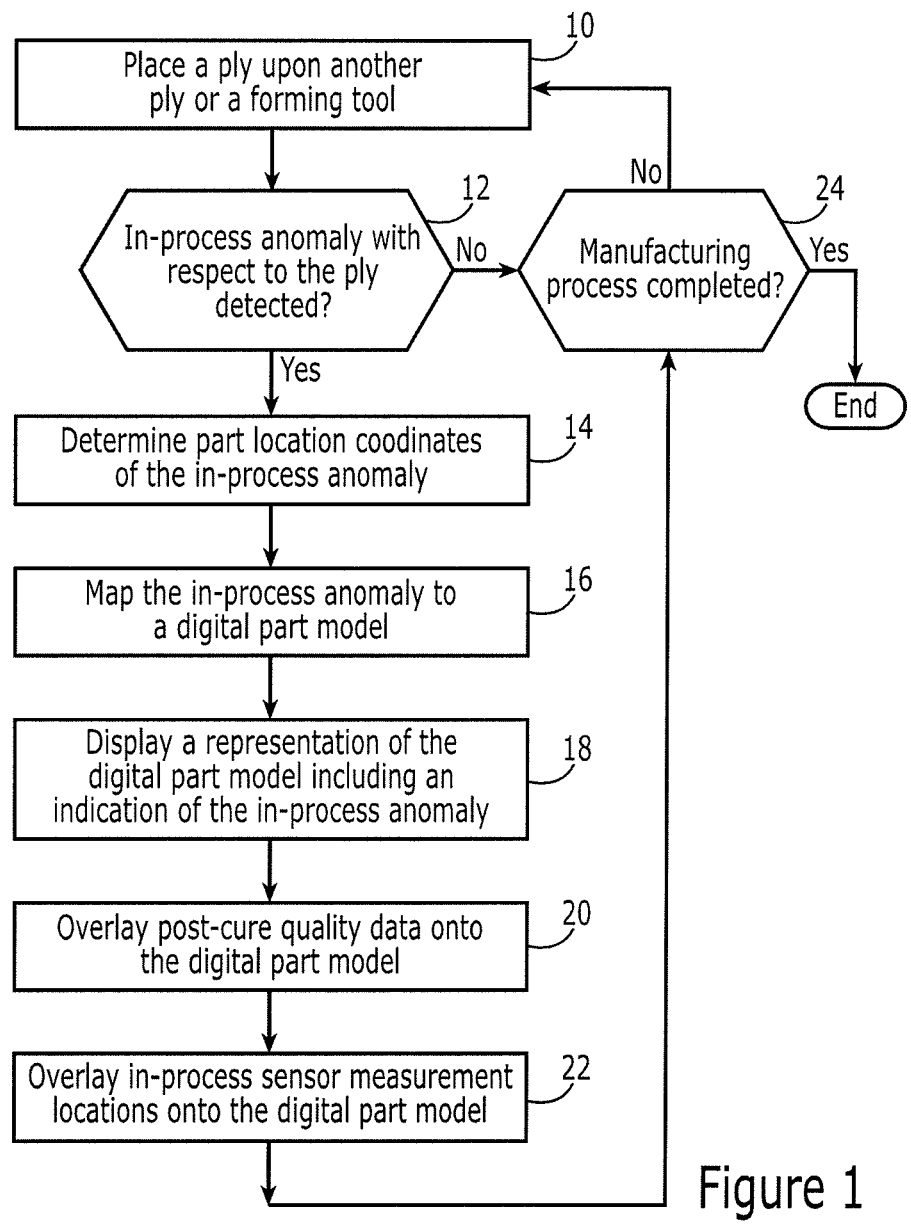
Figure 2:
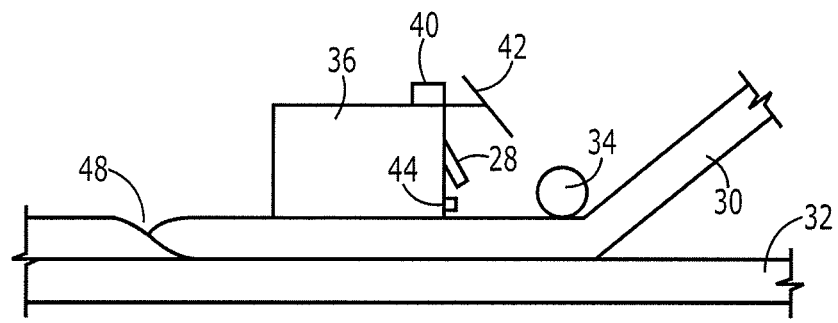
Figure 3:
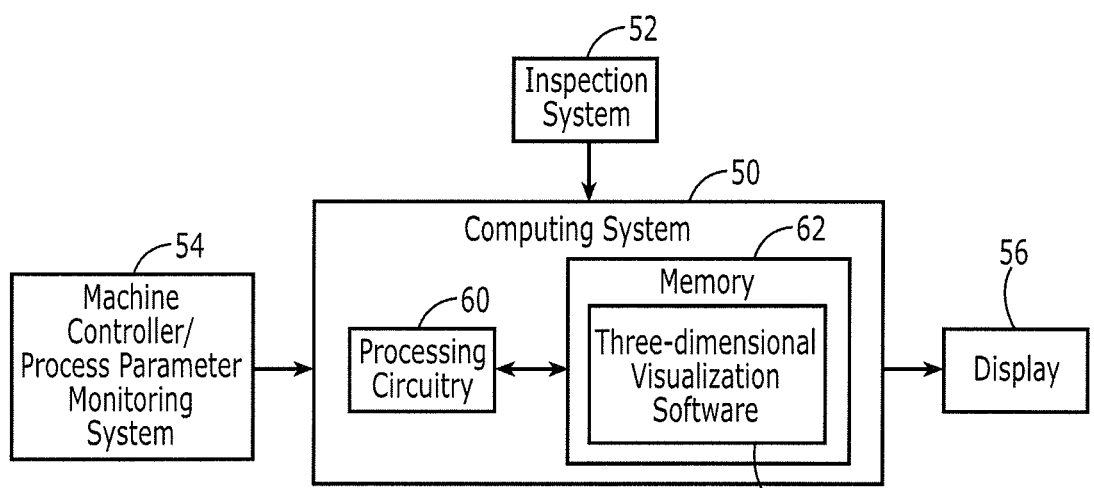
Figure 4:
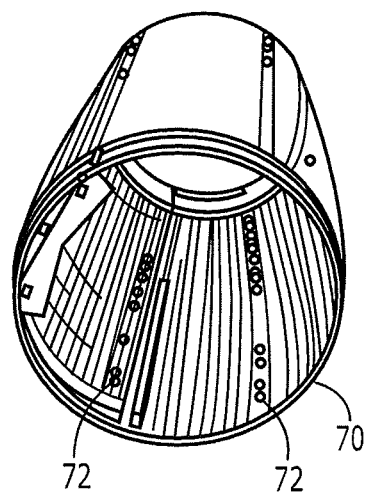

Having thus described aspects of the present disclosure in general terms, reference will now be made to the accompanying drawings, which are not necessarily drawn to scale, and wherein:

FIG. 1 is a flowchart depicting operations performed in accordance with an example embodiment of the present disclosure;

FIG. 2 is a side view of the placement of a ply of a composite part and the detection of an in-process anomaly during the placement of the ply in accordance with an example embodiment of the present disclosure;

FIG. 3 is a block diagram of a system for inspecting a composite part during manufacture in accordance with an example embodiment of the present disclosure; and FIG. 4 is a representation of a digital part model including indications of in-process anomalies that may be displayed in accordance with an example embodiment of the present disclosure.

DETAILED DESCRIPTION

The present disclosure now will be described more fully hereinafter with reference to the accompanying drawings, in which some, but not all aspects are shown. Indeed, the disclosure may be embodied in many different forms and should not be construed as limited to the aspects set forth herein. Rather, these aspects are provided so that this disclosure will satisfy applicable legal requirements. Like numbers refer to like elements throughout.

A system, method and computer-readable storage medium are provided for inspecting a composite part during manufacture. The system, method and computer-readable storage medium may be configured to inspect a variety of composite parts. For example, the system, method and computer-readable storage medium of an example embodiment may be configured to inspect the barrel sections of the fuselage of an aircraft during manufacture thereof. However, the system, method and computer-readable storage medium may be configured to inspect other composite parts of an aircraft or other aerospace vehicle during manufacture or to inspect composite parts manufactured for other applications. If one or more anomalies are identified during the inspection, a determination may be made as to how the anomalies are to be addressed and, if desired, an anomaly may be repaired prior to completion of the manufacturing process.

The composite part may be formed of a plurality of plies placed one upon another. A ply may include a tow, a tape or other form of composite material. The composite material may include a plurality of fibers embedded in a resin matrix with the type of fibers and other parameters associated with the fibers and the resin selected based upon the desired properties of the resulting composite part. With reference to block 10 of FIG. 1, a composite part may be manufactured by placing a ply, such as upon another ply, a forming tool or the like. The ply may be placed in various manners although the ply may be placed by hand or the ply may be placed in an automated manner, such as by being laid up by an automated tow placement system or an automated tape placement system. In conjunction with the placement of a ply, the ply may be subjected to a compacting force that serves to force the ply toward the underlying ply or forming tool. For example, a compaction roller may serve to apply the compacting force to the ply during its placement.

As shown in block 12 of FIG. 1, the method of an example embodiment may detect an in-process anomaly with respect to the ply of the composite part during placement of the ply. More specifically, the methods and systems described herein may be used to detect an in-process anomaly, in real-time, while the ply is being placed or laid down by an automated tow placement system. Various types of in-process anomalies may be detected with respect to the ply of the composite part including, for example, dropped tows, untacked tows, tow gaps, twists, overlaps and the presence of FOD. In an instance in which an in-process anomaly is not detected with respect to a ply of the composite part, a determination may be made as to whether the manufacturing process for the composite part has been completed, such as in an instance in which each of the plies of the composite part has been placed. See block 24 of FIG. 1. In an instance in which the manufacturing process has been completed, the inspection process may correspondingly also be concluded. However, if the manufacturing process has not been completed and one or more additional plies remain to be placed, the process may be repeated so as to ensure that each subsequently placed ply is similarly inspected during its placement in order to detect in-process anomalies with respect to the subsequent plies of the composite part.

An in-process anomaly may be detected in various manners. For example, an inspection system may be utilized in order to detect the in-process anomaly with respect to the ply of the composite part during manufacture. Various types of inspection systems may be utilized. In an example embodiment, the inspection system may include a vision based inspection system to scan a surface of the ply of the composite part during placement of the ply. As shown in FIG. 2, a ply 30 may be placed upon an underlying ply 32, a forming tool or the like. In this regard, a compaction roller 34 may engage the ply 30 and apply a compacting force urging the ply 30 toward the underlying ply 32. During placement of the ply 30, an inspection system, such as a vision based inspection system 36, may scan the surface of the ply 30 in order to detect an in-process anomaly 48, such as a twist as shown by way of example in FIG. 2.

A vision based inspection system 36 may include one or more sources of illumination for illuminating a portion of the ply 30, such as the portion of the ply 30 immediately downstream of the compaction roller 34. In this regard, the vision based inspection system 36 may include a solid-state line laser 38 that directs a line of illumination across a ply, such as in a widthwise direction, as the ply appears from beneath the compaction roller. The vision based inspection system 36 may also include a camera 40 for capturing images of the light that returns from the surface of the ply 30. To permit the camera 40 to be spaced further from the surface of the ply 30 undergoing inspection, the vision based inspection system 36 may also include a mirror 42 that reflects the light returning from the ply to the camera 40.

Certain types of anomalies may be most effectively identified as a result of interrogation by a laser line, such as tow gaps, missing tows, overlaps and twists. However, other types of anomalies, such as the presence of FOD, are more effectively identified based upon an illumination of a broader area. As such, a vision based inspection system 36 may also or alternatively include a more dispersed illumination source, such as a light emitting diode (LED) light bar 44, for illuminating an area of the ply 30 proximate the compaction roller 34, such as the portion of the ply immediately downstream of the compaction roller. The camera 40 may, in turn, capture images of the more broadly illuminated area such that at least certain types of anomalies, such as the presence of FOD, may be identified from an analysis therefrom.

The vision based inspection system 36 may be configured to move across the surface of the ply 30, such as in concert with an automated tow placement system or an automated tape placement system, and to sequentially illuminate different portions of the ply and, in turn, to capture images of the light returning from the different portions of the ply. The vision based inspection system or a computing system that is responsive to the vision based inspection system, such as computing system 50 as described below, may analyze the images captured by the camera 40. The vision based inspection system or a computing system that is responsive to the vision based inspection system may analyze the images, such as by comparing the images of adjacent portions of the ply, in order to identify changes in the images that are likely attributable to anomalies that alter the surface topography of the composite part. As such, a vision based inspection system may detect in-process anomalies 48 with respect to a ply of the composite part during placement of the ply.

As noted above, however, other types of inspection systems may alternatively be utilized to detect an in-process anomaly 48 with respect to ply 30 of the composite part. Additionally, a nondestructive inspection system, such as an ultrasonic or thermographic inspection system, may interrogate the ply following fabrication and cure with ultrasonic or thermal signals, respectively, and may analyze the response in order to detect an in-process anomaly with respect to the ply, such as foreign material that was trapped in the laminate prior to cure, porosity occurring as a result of the cure process or the like.

As shown in block 14 of FIG. 1, the inspection method of an example embodiment also includes determining part location coordinates of the in-process anomaly 48 with respect to the ply 30 of a composite part. In this regard, the inspection system may include a computing system. As shown in FIG. 3, the computing system 50 may be responsive to the inspection system 52, such as the vision based inspection system 36 shown in FIG. 2, a nondestructive inspection system or the like, and may be configured to determine part location coordinates of the in-process anomaly with respect to the ply of the composite part. As discussed below, the part location coordinates may be determined by initially determining machine axis coordinates of the in-process anomaly with respect to the ply 30 of the composite part and thereafter converting the machine axis coordinates to part location coordinates of the in-process anomaly with respect to the composite part itself.

Although the computing system 50 may be configured in a variety of different manners, FIG. 3 depicts an example of a computing system that may be embodied by a server, a personal computer, a tablet computer or the like. However, other types of computing systems may embody the method and computer program product of an embodiment of the present disclosure.

Regardless of the instantiation of the computing system 50, the computing system may be configured in various manners. By way of example, the computing system of one embodiment is shown in FIG. 3 to include or otherwise be associated with a processing circuitry 60 and memory 62 for performing the various functions herein described. The processing circuitry may, for example, be embodied as various means including one or more microprocessors, one or more coprocessors, one or more multi-core processors, one or more controllers, one or more computers, various other processing elements including integrated circuits such as, for example, an ASIC (application specific integrated circuit) or FPGA (field programmable gate array), or some combination thereof. In some example embodiments, the processing circuitry is configured to execute instructions stored in the memory or otherwise accessible to the processing circuitry. These instructions, when executed by the processing circuitry, may cause the computing system to perform one or more of the functionalities described herein. As such, the computing system 50 may comprise an entity capable of performing operations according to embodiments of the present disclosure while configured accordingly. Thus, for example, when the processing circuitry 60 is embodied as an ASIC, FPGA or the like, the processor and, correspondingly, the computing system may comprise specifically configured hardware for conducting one or more operations described herein. Alternatively, as another example, when the processing circuitry is embodied as an executor of instructions, such as may be stored in the memory, the instructions may specifically configure the processing circuitry and, in turn, the computing system to perform one or more algorithms and operations described herein.

The memory 62 may include, for example, volatile and/or non-volatile memory. The memory may comprise, for example, a hard disk, random access memory, cache memory, flash memory, an optical disc (e.g., a compact disc read only memory (CD-ROM), digital versatile disc read only memory (DVD-ROM), or the like), circuitry configured to store information, or some combination thereof. In this regard, the memory may comprise any non-transitory computer readable storage medium. The memory may be configured to store information, data, applications, instructions, or the like for enabling the computing system 50 to carry out various functions in accordance with example embodiments of the present disclosure. For example, the memory may be configured to store program instructions for execution by the processing circuitry 60.

In regards to the determination of part location coordinates of the in-process anomaly 48 with respect to the ply 30 of the composite part, the computing system 50 may be configured to obtain machine axis coordinates of the in-process anomaly with respect to the ply of a composite part. In this regard, the machine axis coordinates define the coordinates of the automated tow placement system or an automated tape placement system at the time at which that portion of the ply that includes the in-process anomaly that has been detected was placed. The machine axis coordinates are defined in terms of the coordinate axes defined by the automated tow or tape placement system. As shown in FIG. 3, the computing system may obtain the machine axis coordinates of the in-process anomaly from a machine controller or a process parameter monitoring system 54, such as the General Electric Proficy Historian™ system. In this regard, the machine controller of an automated tow placement system or an automated tape placement system controls the placement of the ply and, as such, maintains a record of the machine axis coordinates during placement of each portion of the ply. Additionally or alternatively, a process parameter monitoring system, such as the General Electric Proficy Historian™ system, does not control the placement of the ply, but similarly maintains a record of the machine axis coordinates of an automated tow placement system or an automated tape placement system during the placement of each portion of the ply.

In order to determine the part location coordinates, the computing system 50 may also be configured to convert the machine axis coordinates provided by a machine controller or a process parameter monitoring system 54 to a part location coordinates. For example, in an instance in which the composite part that is being manufactured is an aircraft, the computing system may be configured to convert the machine axis coordinates to aircraft coordinates.

As shown in block 16 of FIG. 1, the method for inspecting a composite part during manufacture may also map the in-process anomaly 48 to a digital part model based upon the part location coordinates. In the embodiment depicted in FIG. 3, for example, the computing device may be configured to map the in-process anomaly to a digital part model based upon the part location coordinates. In this regard, a digital part model may be predefined and may be stored, such as by memory 62. A digital part model may be defined in terms of part location coordinates with the digital part model being provided by an application such as computer added three-dimensional interactive application (CATIA) software to three-dimensional visualization software 64, such as NLIGN Analytics™ software, stored, for example by memory 62 as shown in FIG. 3 that facilitates presentation of the digital part model. As such, the computing device of this example embodiment is configured to map the in-process anomaly to the digital part model by providing the part location coordinate for the in-process anomaly to the three-dimensional visualization software that overlays the representation of the in-process anomaly onto the digital part model.

As shown in block 18 of FIG. 1, the method for inspecting a composite part during manufacture may also include displaying a representation of the digital part model including an indication of the in-process anomaly 48 relative thereto. With respect to the embodiment of the system depicted in FIG. 3, the system may also include a display 56, responsive to the computing system 50. Thus, the computing system may be configured to provide the digital part model including the in-process anomaly mapped thereto to the display. In response, the display may be configured to present a representation of the digital part model including an indication of the in-process anomaly relative thereto. The digital part model may be represented in various manners, but, in one embodiment, may be a three-dimensional rendering, such as a wire frame rendering or other type of rendering, of the composite part. The indication of the in-process anomaly may be displayed upon the representation of the digital part model. Various indications of an in-process anomaly may be provided including, for example, a dot, a flag or other visual indicia of the in-process anomaly placed relative to the digital part model to illustrate the location of the in-process anomaly. As shown in FIG. 4, for example, a digital part model 70 of a barrel section of the fuselage of an aircraft is depicted. Each of the in-process anomalies that have been detected with respect to a ply of the barrel section are indicated in FIG. 4 by a corresponding dot 72 at a location that corresponds to the location of a respective in-process anomaly with respect to the barrel section.

In some embodiments, the computing device 50 may be configured to provide additional information regarding an in-process anomaly 48 in response to user selection of the indication, e.g., the dot 72, associated with the in-process anomaly. A variety of additional information may be provided including, for example, information regarding the type of in-process anomaly, a photograph of the in-process anomaly, etc.

Based upon the indications 72 of the in-process anomalies 48 that are presented upon the representation of the digital part model that is displayed, a technician may efficiently determine the manner in which each of the in-process anomalies is to be addressed. In this regard, the disposition of the in-process anomalies may be based at least in part upon the relative position of the anomaly with respect to the composite part such that the presentation of an indication of an in-process anomaly upon the representation of the digital part model facilitates the determination as to whether the location of the in-process anomaly merits repair and, if so, the type of repair to be undertaken.

Additionally, the determination as to the manner in which to address an in-process anomaly 48 may be at least partially dependent upon the relative location of in-process anomalies detected in other plies of the composite part that have been previously placed upon the forming tool and that have not been repaired. Thus, the representation of the digital part model may provide an indication 72 of the in-process anomalies 48 detected with respect to the ply 30 currently being placed, and may also provide an indication of other anomalies previously detected with respect to other plies of the composite part. The indications of the anomalies may be different, such as by being of a different color, being of a different shape or the like, depending upon the ply in which the anomaly was detected. As such, a technician may efficiently determine the relative location of an in-process anomaly for the ply that is currently being placed relative to the anomalies that were detected in other plies of the composite part and that were not repaired. As such, a technician may utilize the relative locations of the anomalies in the different plies in order to determine the manner in which to address the in-process anomaly with respect to the ply of the composite part that was most recently been placed.

Based upon this determination, one or more of the anomalies 48 in the ply 30 that was most recently been placed may be addressed, such as by being repaired, prior to placing the next overlying ply thereupon. As a result of the automated detection and display of the in-process anomaly relative to a digital part model, a determination of the in-process anomalies to be repaired may be performed in an efficient manner, thereby also permitting repairs to be affected in an efficient manner and allowing the manufacturing process to proceed more expeditiously.

In conjunction with the detection of the in-process anomaly 48, the type of in-process anomaly may be determined, such as by the inspection system 52, the computing system 50 or the like. In this regard, different types of in-process anomalies, such as dropped tows, untacked tows, tow gaps, twists, overlaps and the presence of FOD, may be individually determined. In this example embodiment, the computing system in cooperation with the display 54 may be configured to assign different visual indications to different types of in-process anomalies, thereby permitting a technician to readily distinguish between different types of anomalies which may be addressed in different manners. For example, the visual indications for the different types of in-process anomalies may have different colors, different shapes, different text associated therewith or the like in order to distinguish the different types of in-process anomalies. With respect to the representation of a digital part model in FIG. 4, the indications of different types of in-process anomalies may be represented by circles having different shades of gray with each shade of gray representative of a different type of in-process anomaly that has been detected.

In some embodiments, additional information may be provided concurrent with the display of the digital part model 70 and the indications 72 of the in-process anomalies. As shown in block 20 of FIG. 1, for example, post-cure quality data, such as may be stored by memory 62, may be overlaid onto the digital part model concurrent with the indications of the in-process anomalies. The post-cure quality data may be provided, for example, by a nondestructive inspection system, such as an ultrasonic inspection system. Additionally or alternatively, in-process sensor measurement locations (and data), such as may also be stored by memory, may be overlaid onto the digital part model concurrent with the indications of the in-process anomalies. See block 22 of FIG. 1. The locations of the sensors may be expressed in tool coordinates with the tool coordinates being transformed to part location coordinates in order to accurately overlay the sensor measurement locations onto the digital part model. The sensors may be configured to measure various parameters including, for example, sensors associated with monitoring bag integrity for vacuum bag utilized during the subsequent autoclave curing of the composite part and/or temperature and pressure sensors for use during the subsequent autoclave curing. Based upon this additional information, a technician may be able to make more well informed decisions regarding the manner in which to address the in-process anomalies that have been detected, thereby improving the efficiency with which the composite part is manufactured. For example, the simultaneous display of the digital part model with the indications of the in-process anomalies, the post-cure quality data and/or the in-process sensor measurement data may permit relationships and trends to be established between the occurrence of an in-process anomaly and sensor and/or ultrasonic data, such as anomalous sensor and/or ultrasonic data.

As described above, FIG. 1 illustrates a flowchart of a system, method, and computer program product according to example embodiments of the present disclosure. It will be understood that each block of the flowchart, and combinations of blocks in the flowchart, may be implemented by various means, such as hardware and/or a computer program product comprising one or more computer-readable storage mediums having computer readable program instructions stored thereon. For example, one or more of the procedures described herein may be embodied by computer program instructions of a computer program product. In this regard, the computer program product(s) which embody the procedures described herein may be stored by one or more memory devices 62 of a computing system 50 and executed by a processing circuitry 60 of the computing system. In some embodiments, the computer program instructions comprising the computer program product(s) which embody the procedures described above may be stored by a plurality of memory devices. As will be appreciated, any such computer program product may be loaded onto a computer or other programmable apparatus to produce a machine, such that the computer program product including the instructions which execute on the computer or other programmable apparatus creates means for implementing the functions specified in the flowchart blocks. Further, the computer program product may comprise one or more computer-readable memories on which the computer program instructions may be stored such that the one or more computer-readable memories can direct a computer or other programmable apparatus to function in a particular manner, such that the computer program product comprises an article of manufacture which implements the function specified in the flowchart blocks. The computer program instructions of one or more computer program products may also be loaded onto the computing system or other programmable apparatus to cause a series of operations to be performed on the computing system or other programmable apparatus to produce a computer-implemented process such that the instructions which execute on the computing system or other programmable apparatus implement the functions specified in the flowchart blocks.

Accordingly, blocks or steps of the flowchart support combinations of means for performing the specified functions and combinations of steps for performing the specified functions. It will also be understood that one or more blocks of the flowchart, and combinations of blocks in the flowchart, may be implemented by special purpose hardware-based computer systems which perform the specified functions or steps, or combinations of special purpose hardware and computer program products.

The above described functions may be carried out in many ways. For example, any suitable means for carrying out each of the functions described above may be employed to carry out embodiments of the present disclosure. In one embodiment, a suitably configured computing system 50 may provide all or a portion of the elements of the present disclosure. In another embodiment, all or a portion of the elements may be configured by and operate under control of a computer program product. The computer program product for performing the methods of embodiments of the present disclosure includes a computer-readable storage medium, such as the non-volatile storage medium, and computer-readable program code portions, such as a series of computer instructions, embodied in the computer-readable storage medium.

Many modifications and other aspects of the disclosure set forth herein will come to mind to one skilled in the art to which this disclosure pertains having the benefit of the teachings presented in the foregoing descriptions and the associated drawings. Therefore, it is to be understood that the disclosure is not to be limited to the specific aspects disclosed and that modifications and other aspects are intended to be included within the scope of the appended claims. Although specific terms are employed herein, they are used in a generic and descriptive sense only and not for purposes of limitation.

That which is claimed:

1. A method for inspecting a composite part during manufacture, the method comprising:
   detecting an in-process anomaly with respect to a ply of the composite part during placement of the ply;
   determining part location coordinates of the in-process anomaly with respect to the ply of the composite part, wherein determining the part location coordinates comprises obtaining machine axis coordinates of the in-process anomaly which define coordinates of an automated tow placement system or an automated tape placement system at a time at which that portion of the ply that includes the in-process anomaly that has been detected was placed, wherein the machine axis coordinates are obtained from a machine controller or a process parameter monitoring system, and wherein determining the part location coordinates further comprise converting the machine axis coordinates to the part location coordinates;
   mapping the in-process anomaly to a digital part model based upon the part location coordinates; and
   displaying a representation of the digital part model including an indication of the in-process anomaly relative thereto.

2. A method according to claim 1 wherein detecting the in-process anomaly comprises scanning a surface of the ply of the composite part during placement of the ply with a vision based inspection system.

3. A method according to claim 1 wherein mapping the in-process anomaly to the digital part model comprises providing the part location coordinates for the in-process anomaly to three-dimensional visualization software that overlays the representation of the in-process anomaly onto the digital part model.

4. A method according to claim 1 wherein detecting the in-process anomaly comprises determining a type of in-process anomaly from among different types of anomalies including dropped tows, untacked tows, tow gaps, twists, overlaps or a presence of foreign object debris, and wherein displaying the representation of the digital part model comprises assigning different visual indications to different types of in-process anomalies.

5. A method according to claim 1 wherein displaying the representation of the digital part model further comprises overlaying post-cure quality data onto the digital part model concurrent with the indications of the in-process anomalies.

6. A method according to claim 1 wherein displaying the representation of the digital part model further comprises overlaying in-process sensor measurement locations onto the digital part model concurrent with the indications of the in-process anomalies.

7. A system for inspecting a composite part during manufacture, the system comprising:
   an inspection system configured to detect an in-process anomaly with respect to a ply of the composite part during placement of the ply;
   a computing system comprising processing circuitry configured to determine part location coordinates of the in-process anomaly detected by the inspection system with respect to the ply of the composite part, wherein the computing system is configured to determine the part location coordinates by obtaining machine axis coordinates of the in-process anomaly which define coordinates of an automated tow placement system or an automated tape placement system at a time at which that portion of the ply that includes the in-process anomaly that has been detected was placed, wherein the machine axis coordinates are obtained from a machine controller or a process parameter monitoring system, and wherein the computing system is further configured to determine the part location coordinates by converting the machine axis coordinates to the part location coordinates wherein the computing system is also configured to map the in-process anomaly to a digital part model based upon the part location coordinates; and a display, responsive to the computing system, configured to present a representation of the digital part model including an indication of the in-process anomaly relative thereto.

8. A system according to claim 7 wherein the inspection system comprises a vision based inspection system configured to scan a surface of the ply of the composite part during placement of the ply.

9. A system according to claim 7 wherein the computing system is configured to map the in-process anomaly to the digital part model by providing the part location coordinates for the in-process anomaly to three-dimensional visualization software that overlays the representation of the in-process anomaly onto the digital part model.

10. A system according to claim 7 wherein the computing system is further configured to determine a type of in-process anomaly from among different types of anomalies including dropped tows, untacked tows, tow gaps, twists, overlaps or a presence of foreign object debris, and wherein the display is further configured to assigning different visual indications to different types of in-process anomalies.

11. A system according to claim 7 wherein the display is further configured to overlay post-cure quality data onto the digital part model concurrent with the indications of the in-process anomalies.

12. A system according to claim 7 wherein the display is further configured to overlay in-process sensor measurement locations onto the digital part model concurrent with the indications of the in-process anomalies.

13. A non-transitory computer-readable storage medium for inspecting a composite part during manufacture, the computer-readable storage medium having computer-readable program code portions stored therein that in response to execution cause a computing system to:
receive information regarding an in-process anomaly with respect to a ply of the composite part during placement of the ply;
determine part location coordinates of the in-process anomaly with respect to the ply of the composite part, wherein the computing system is caused to determine the part location coordinates by obtaining machine axis coordinates of the in-process anomaly which define coordinates of an automated tow placement system or an automated tape placement system at the time at which that portion of the ply that includes the in-process anomaly that has been detected was placed, wherein the machine axis coordinates are obtained from a machine controller or a process parameter monitoring system, and wherein the computing system is further caused to determine the part location coordinates by converting the machine axis coordinates to the part location coordinates;
map the in-process anomaly to a digital part model based upon the part location coordinates; and
cause a representation to be presented of the digital part model including an indication of the in-process anomaly relative thereto.

14. A computer-readable storage medium according to claim 13 wherein the computer-readable program code portions configured to map the in-process anomaly to the digital part model comprises computer-readable program code portions configured to provide the part location coordinates for the in-process anomaly to three-dimensional visualization software that overlays the representation of the in-process anomaly onto the digital part model.

15. A computer-readable storage medium according to claim 13 wherein the computer-readable program code portions configured to detect the in-process anomaly comprise computer-readable program code portions configured to determine a type of in-process anomaly from among different types of anomalies including dropped tows, untacked tows, tow gaps, twists, overlaps or a presence of foreign object debris, and wherein the computer-readable program code portions configured to display the representation of the digital part model comprise computer-readable program code portions configured to assign different visual indications to different types of in-process anomalies.

16. A computer-readable storage medium according to claim 13 wherein the computer-readable program code portions configured to display the representation of the digital part model further comprise computer-readable program code portions configured to overlay post-cure quality data onto the digital part model concurrent with the indications of the in-process anomalies.

17. A computer-readable storage medium according to claim 13 wherein the computer-readable program code portions configured to display the representation of the digital part model further comprise computer-readable program code portions configured to overlay in-process sensor measurement locations onto the digital part model concurrent with the indications of the in-process anomalies.

* * * * *